(12) United States Patent
Chen et al.

(10) Patent No.: US 9,050,047 B2
(45) Date of Patent: Jun. 9, 2015

(54) RESISTANCE FEEDBACK LARYNGOSCOPE

(71) Applicants: Hung-Shu Chen, Kaohsiung (TW); Hsu-Fu Wu, Kaohsiung (TW); Tuo-Hou Chang, Kaohsiung (TW)

(72) Inventors: Hung-Shu Chen, Kaohsiung (TW); Hsu-Fu Wu, Kaohsiung (TW); Tuo-Hou Chang, Kaohsiung (TW)

(73) Assignee: Alliance Global Technology Corp., Kaohsiung (TW)

( * ) Notice: Subject to any disclaimer, the term of this patent is extended or adjusted under 35 U.S.C. 154(b) by 164 days.

(21) Appl. No.: 13/952,705

(22) Filed: Jul. 29, 2013

(65) Prior Publication Data

US 2015/0031957 A1     Jan. 29, 2015

(51) Int. Cl.
    *A61B 1/267* (2006.01)
(52) U.S. Cl.
    CPC ...................................... *A61B 1/267* (2013.01)
(58) Field of Classification Search
    CPC .......................................................... A61B 1/267
    USPC .......................... 600/190, 193, 194, 196, 197
    See application file for complete search history.

(56) References Cited

U.S. PATENT DOCUMENTS

| 4,360,008 A * | 11/1982 | Corazzelli, Jr. ............... 600/194 |
| 5,584,795 A * | 12/1996 | Valenti .......................... 600/196 |
| 6,251,069 B1 * | 6/2001 | Mentzelopoulos et al. .. 600/196 |

OTHER PUBLICATIONS

Min, K.T. et al., Derwent Abstracted Publication No. KR 873929 B1, (2006), entire document, esp. figure, p. 4.*

* cited by examiner

*Primary Examiner* — Pedro Philogene
*Assistant Examiner* — David Comstock
(74) *Attorney, Agent, or Firm* — Alan D. Kamrath; Kamrath IP Lawfirm, P.A.

(57) ABSTRACT

A resistance feedback laryngoscope contains a pushing grip, a trigger pad, a rotary shaft, a first transmitting rod, a second transmitting rod, and a two-step levering blade. The pushing grip includes a curved front side connecting with the two-step levering blade. The two-step levering blade includes a first movable blade, a second movable blade, and a fixed blade. The first transmitting rod and the second transmitting rod connect with the rotary shaft fixed on a drive post with a resilient element. The resilient element has a first foot butting against a locking peg proximate to the drive post and has a second foot being biased against a side piece of the rotary shaft. The trigger pad contacts with the pushing grip and curves upward slightly, and the trigger pad includes an arcuate groove formed therein, a bottom end of the arcuate groove contacts with the side piece of the rotary shaft.

4 Claims, 7 Drawing Sheets

RESISTANCE FEEDBACK LARYNGOSCOPE

FIELD OF THE INVENTION

The present invention relates to a rigid laryngoscope with a resistance feedback mechanism and a two-step levering blade in which the pushing grip pushes the trigger pad to drive the rotary shaft, and then the first transmitting rod and the second transmitting rod are driven by the rotary shaft so as to actuate the first movable blade and the second movable blade to raise upwardly, thus effectively lifting the larynx and preventing the teeth from damage.

BACKGROUND OF THE INVENTION

For an airway management, a tracheal intubation is safest common skill, and a rigid laryngoscope is usually applied in an intubating process.

Yet the tracheal intubation sometimes may cause complications. For example, in the U.S., difficult and failed tracheal intubation is a major cause of anesthesia-related death. Furthermore, dental damage related to tracheal intubation is the adverse event responsible for majority of malpractice claims against anesthesiologists.

With reference to FIG. 1, a conventional laryngoscope 1 is formed in an L shape and contains an arcuately fixed blade 11, so when the laryngoscope 1 is used in an intubating operation, a difficult laryngoscopy may occur, i.e., the medical staff forces onto the laryngoscope 1 laboriously, thereby damaging the patient's teeth.

To solve such a problem, video laryngoscopes are developed to check the patient's throat. However, such improved laryngoscopes are expensive.

The present invention has arisen to mitigate and/or obviate the afore-described disadvantages.

SUMMARY OF THE INVENTION

The primary object of the present invention is to provide a rigid laryngoscope with a resistance feedback mechanism and a two-step levering blade in which the pushing grip pushes the trigger pad to drive the rotary shaft, and then the first transmitting rod and the second transmitting rod are driven by the rotary shaft so as to actuate the first movable blade and the second movable blade to raise upwardly, thus effectively lifting the larynx and preventing the teeth from damage.

To obtain the above objectives, a resistance feedback laryngoscope contains a pushing grip, a trigger pad, a rotary shaft, a first transmitting rod, a second transmitting rod, and a two-step levering blade.

The pushing grip includes a curved front side, and a bottom end of the curved front side of the pushing grip connects with the two-step levering blade. The curved handle allows laryngoscopists to manipulate the laryngoscope under cylindrical grasp with natural position of the wrist to facilitate directly pushing the laryngoscope upward/forward. The two-step levering blade includes a first movable blade fixed on a middle section thereof, a second movable blade mounted on a front end thereof, and a fixed blade. The fixed blade couples with the first transmitting rod and the second transmitting rod, and a front end of the first transmitting rod is coupled with the first movable blade, a front end of the second transmitting rod is connected with the second movable blade, such that the first movable blade and the second movable blade are pushed by the first transmitting rod and the second transmitting rod to raise curvedly.

The first transmitting rod and the second transmitting rod connect with the rotary shaft, the rotary shaft is fixed on a drive post, and the drive post has a resilient element fitted therein, the resilient element has a first foot and a second foot, the first foot of the resilient element abuts against a locking peg proximate to the drive post, and the second foot is biased against a side piece of the rotary shaft.

The trigger pad contacts with two sides of an outer wall of the pushing grip and curves upward slightly, and the trigger pad includes an arcuate groove formed therein, a bottom end of the arcuate groove contacts with the side piece of the rotary shaft.

Thereby, as a sufficient hand grip applying on the handle is essential to maintain the static balance of the forces and moments generated in direct laryngoscopy, the strength of the grip is proportional to the resistance of laryngeal tissue though biofeedback response. The natural gripping force simultaneously trigger the two-step levering blade upward, by which the laryngeal view can be improved. Therefore, the user does not force the laryngoscope excessively to damage patient's teeth and operates the laryngoscope smoothly.

In addition, the laryngoscope is held and pushed into the throat so that the first movable blade and the second movable blade push the throat easily, the user does not have to rotate and force the laryngoscope manually, thus preventing the patient's teeth from being damaged.

DETAILED DESCRIPTION OF THE PREFERRED EMBODIMENTS

Resistance Feedback Laryngoscope

Figure 1:
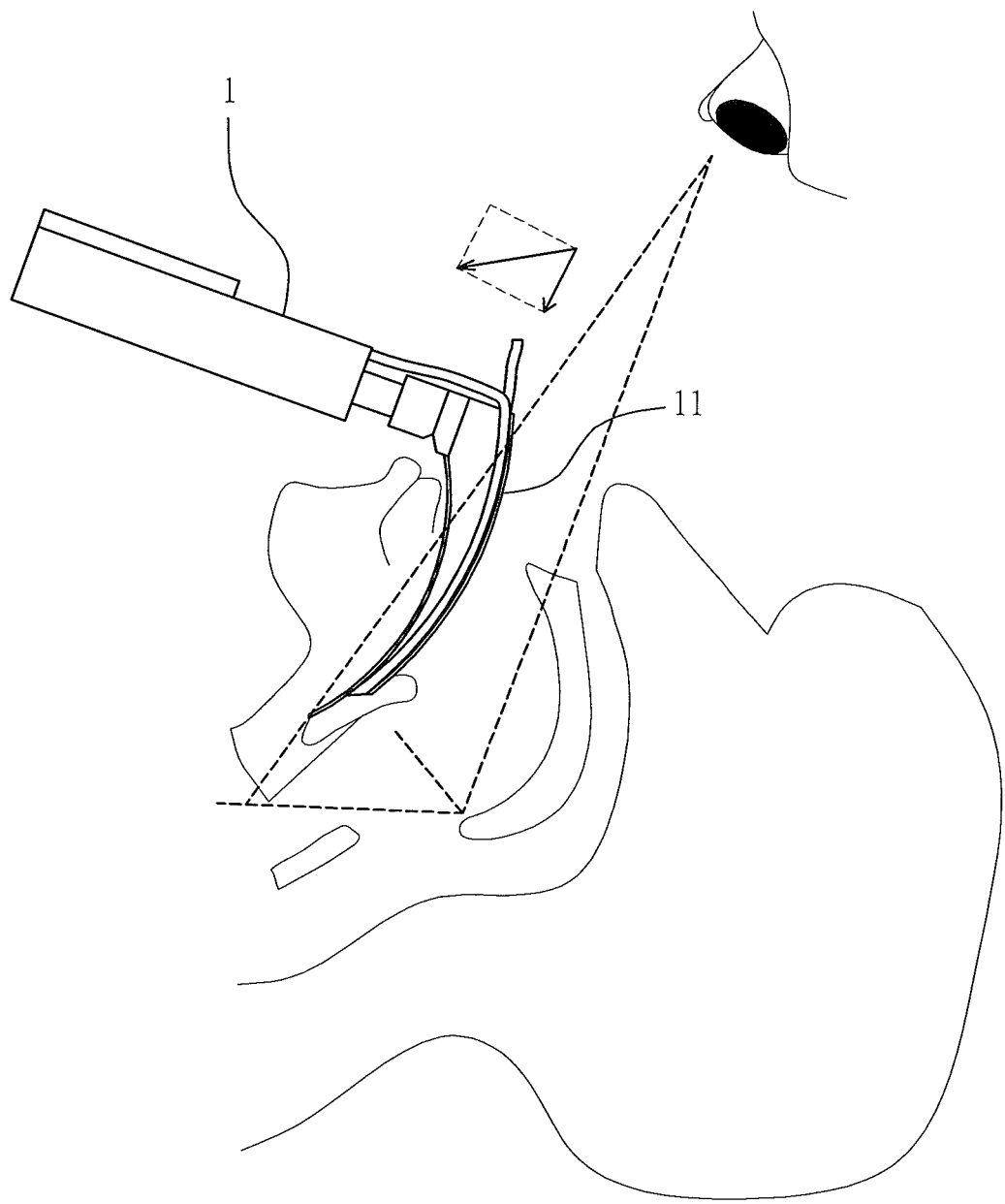
FIG. 1 is a perspective view showing the application of a conventional laryngoscope.
Figure 2:
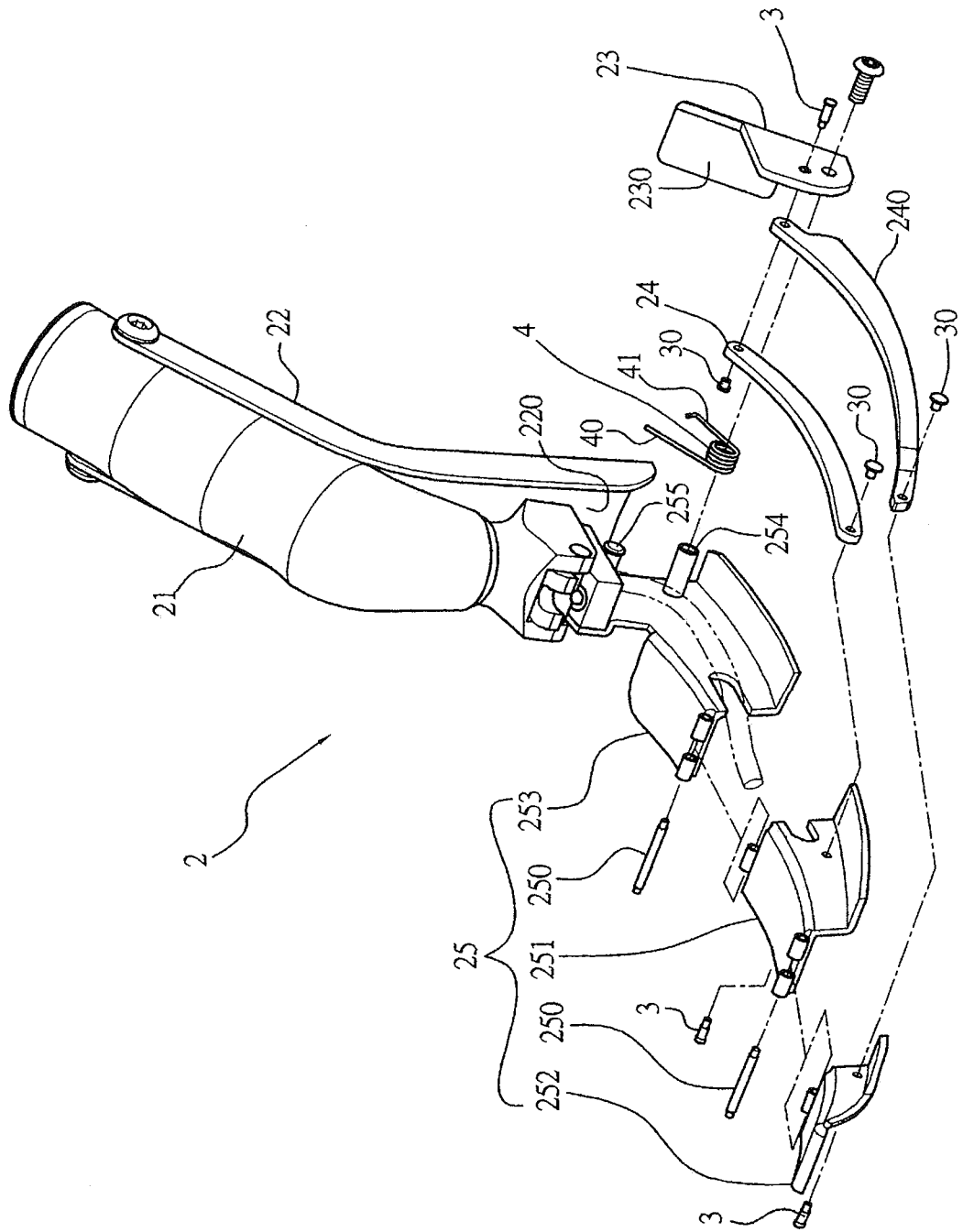
FIG. 2 is a perspective view showing the exploded components of a resistance feedback laryngoscope according to a preferred embodiment of the present invention.

FIG. 2 is a perspective view showing the exploded components of a resistance feedback laryngoscope according to a preferred embodiment of the present invention. A resistance feedback laryngoscope of the present invention comprises a pushing grip 21, a trigger pad 22, a rotary shaft 23, a first transmitting rod 24, a second transmitting rod 240, and a two-step levering blade 25. The pushing grip 21 includes a curved front side, and a bottom end of the curved front side of the pushing grip 21 connects with the two-step levering blade 25, such that a user grips the pushing grip 21 and pushes the two-step levering blade 25 into a patent's mouth. In addition, the two-step levering blade 25 includes a first movable blade 251 fixed on a middle section thereof, a second movable blade 252 mounted on a front end thereof, a fixed blade 253, and a plurality of first bolts 250 for pivoting the first movable blade 251, the second movable blade 252, and the fixed blade 253 together, such that the first movable blade 251 and the second movable blade 252 swing, wherein a length of each first bolt 250 is within 2 to 4 cm.

Figure 3:
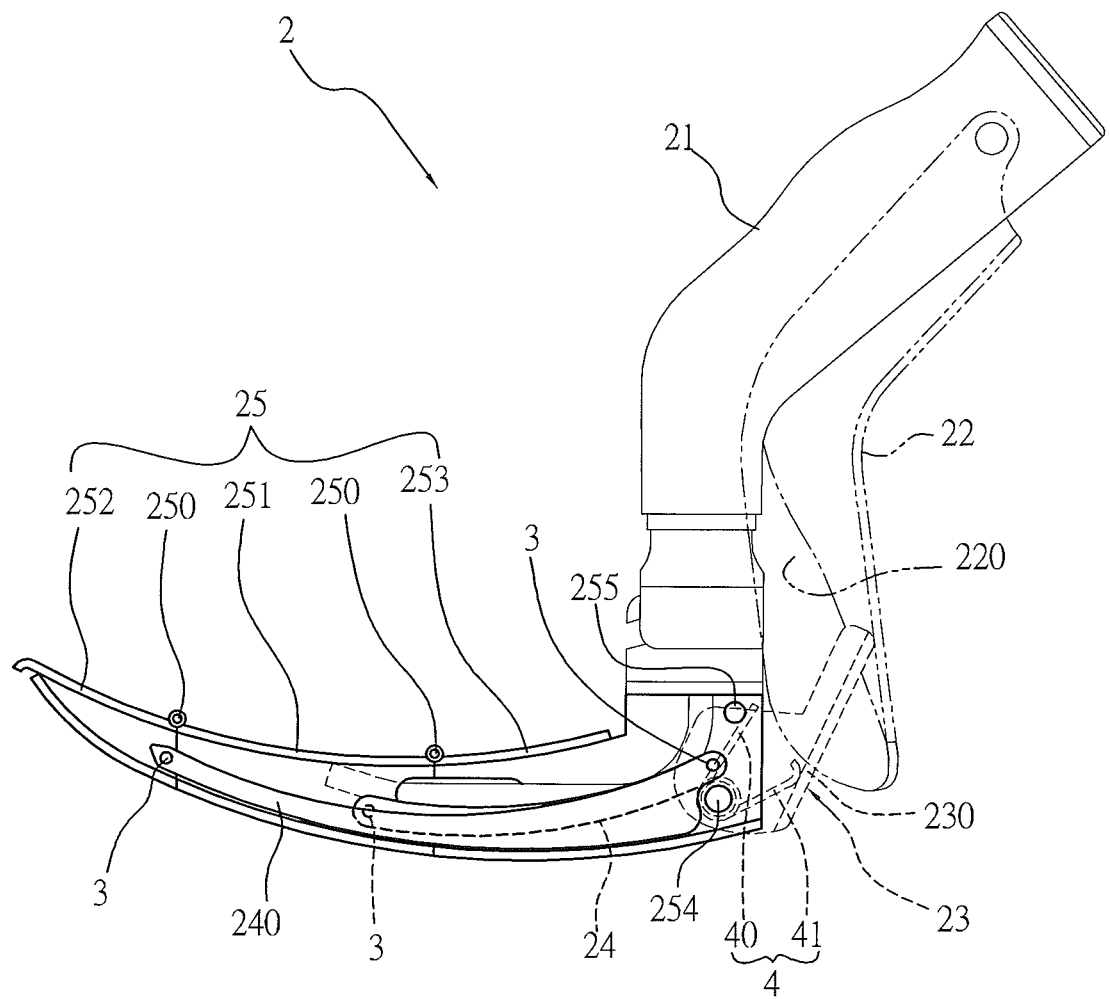
FIG. 3 is a side plan view showing the assembly of the resistance feedback laryngoscope according to the preferred embodiment of the present invention.
Figure 4:
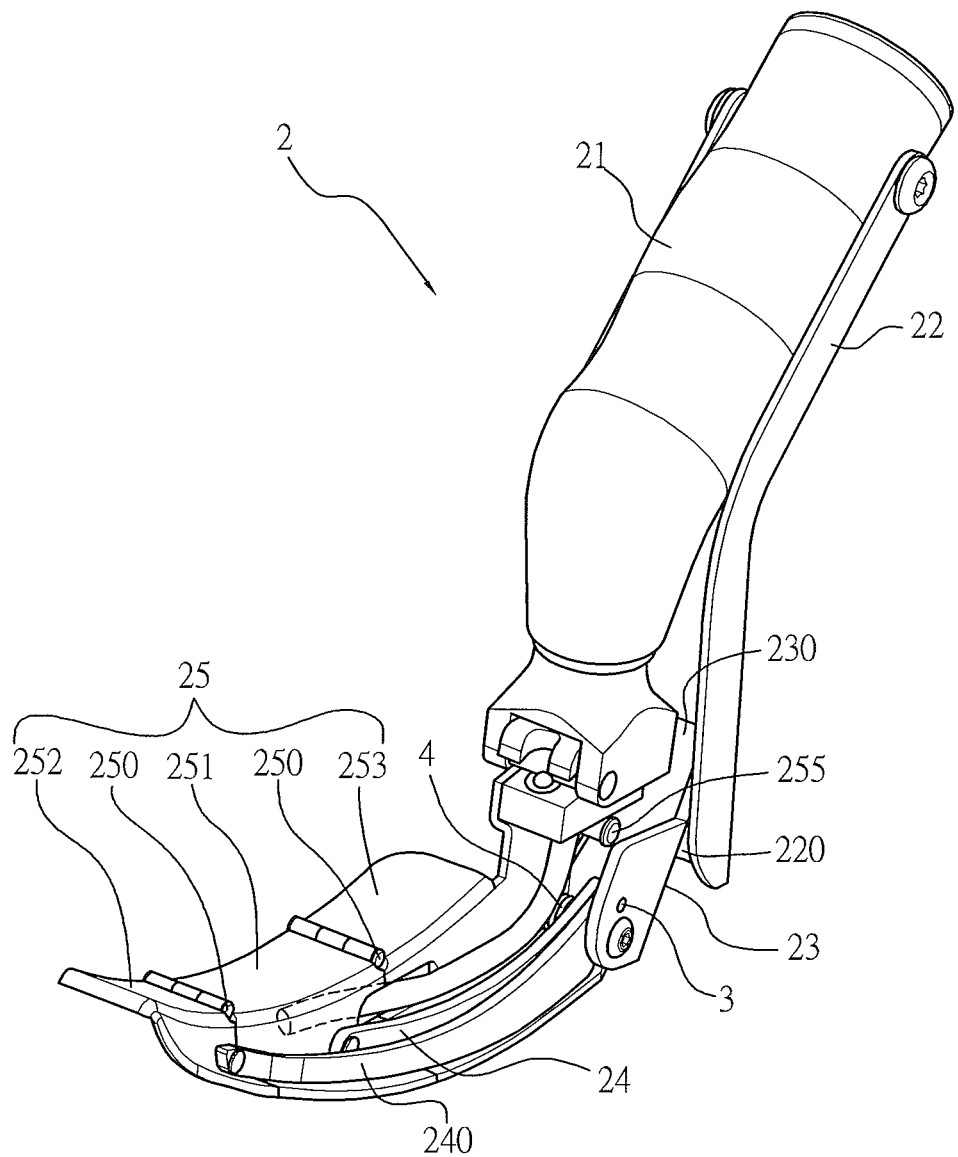
FIG. 4 is a perspective view showing the assembly of the resistance feedback laryngoscope according to the preferred embodiment of the present invention.

The fixed blade 253 couples with the first transmitting rod 24 and the second transmitting rod 240, and a plurality of second bolts 3 are used to connect the first transmitting rod 24, the second transmitting rod 240, and the rotary shaft 23 together, such that the rotary shaft 23 drives the first transmitting rod 24 and the second transmitting rod 240 to swing, and a front end of the first transmitting rod 24 is coupled with the first movable blade 251 by using one of three positioning knobs 30, a front end of the second transmitting rod 240 is connected with the second movable blade 252 by ways of another of the three positioning knobs 30, such that when the first transmitting rod 24 and the second transmitting rod 240 move forward, the first movable blade 251 and the second movable blade 252 are pushed by the first transmitting rod 24 and the second transmitting rod 240 to raise curvedly. The rotary shaft 23 is fixed on a drive post 254, and the drive post 254 has a resilient element 4 fitted therein, the resilient element 4 has a first foot 40 and a second foot 41. Referring to FIG. 3, the first foot 40 abuts against a locking peg 255 proximate to the drive post 254, and the second foot 41 is biased against a side piece 230 of the rotary shaft 23, the trigger pad 22 contacts with two sides of an outer wall of the pushing grip 21 and curves upward slightly. The trigger pad 22 includes an arcuate groove 220 formed therein, and an end edge of the arcuate groove 220 is smooth so as to prevent from damaging the user, and a bottom end of the arcuate groove 220 contacts with the side piece 230 of the rotary shaft 23, thus assembling a laryngoscope 2 as shown in FIG. 4.

As shown in FIG. 3, in an operation of the laryngoscope 2, the arcuate groove 220 of the trigger pad 22 abuts against the side piece 230 of the rotary shaft 23, in the meantime, the blade set 25 forms a sickle-like arcuation, and in an intubating operation, the user holds the pushing grip 21 and presses the trigger pad 22 so that the arcuate groove 220 of the driving member 22 pushes the side piece 230, and then the side piece 230 pushes the second foot 41, the first foot 40 is thereafter biased against the locking peg 255 so that the side piece 230 swings along the drive post 254.

Figure 5:
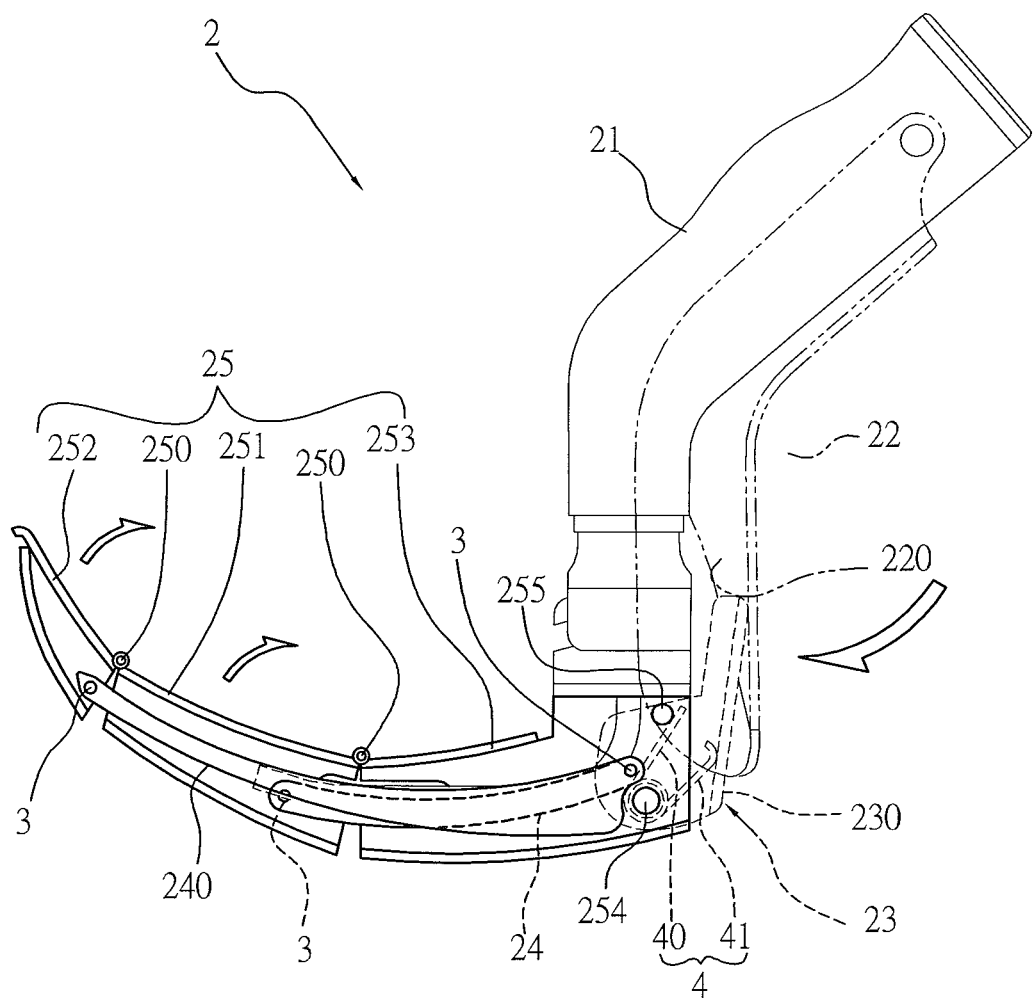
FIG. 5 is a side plan view showing the assembly of the resistance feedback laryngoscope according to the preferred embodiment of the present invention.

Referring further to FIG. 5, when the side piece 230 of the rotary shaft 23 swings, the first transmitting rod 24 and the second transmitting rod 240 are driven by the side piece 230 to move transversely, and then a curved angle generates because the first transmitting rod 24 moves transversely, such that the first transmitting rod 24 pushes the first movable blade 251 upwardly so that the first movable blade 251 curves upward slightly, and the second transmitting rod 40 pushes the second movable blade 252 to raise upwardly at an angle.

Figure 6:
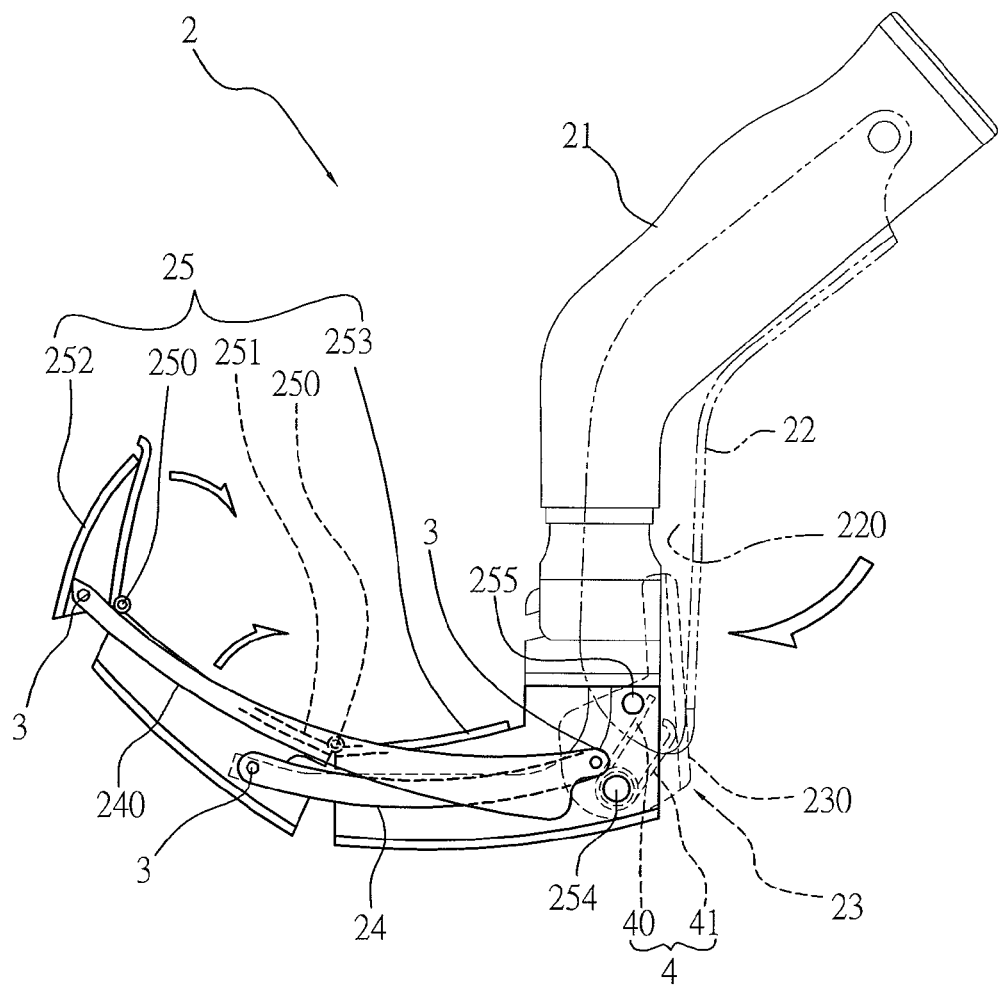
FIG. 6 is another side plan view showing the assembly of the resistance feedback laryngoscope according to the preferred embodiment of the present invention.

When forcing the laryngoscope 2 increasingly, as illustrated in FIG. 6, the first transmitting rod 24 and the second transmitting rod 240 keep bending so that a swing angle of the first movable blade 251 and the second movable blade 252 increases, hence the first movable blade 251 and the second movable blade 252 push a throat of the patient's mouth upwardly, such that the user sees the throat clearly and then has the intubating operation further. Thereby, the user does not force the laryngoscope 2 excessively to damage patient's teeth and operates the laryngoscope 2 smoothly. In addition, the laryngoscope 2 is held and pushed into the throat so that the first movable blade 251 and the second movable blade 252 push the throat easily, the user does not have to rotate and force the laryngoscope 2 manually, thus preventing the patient's teeth from being damaged.

Figure 7:
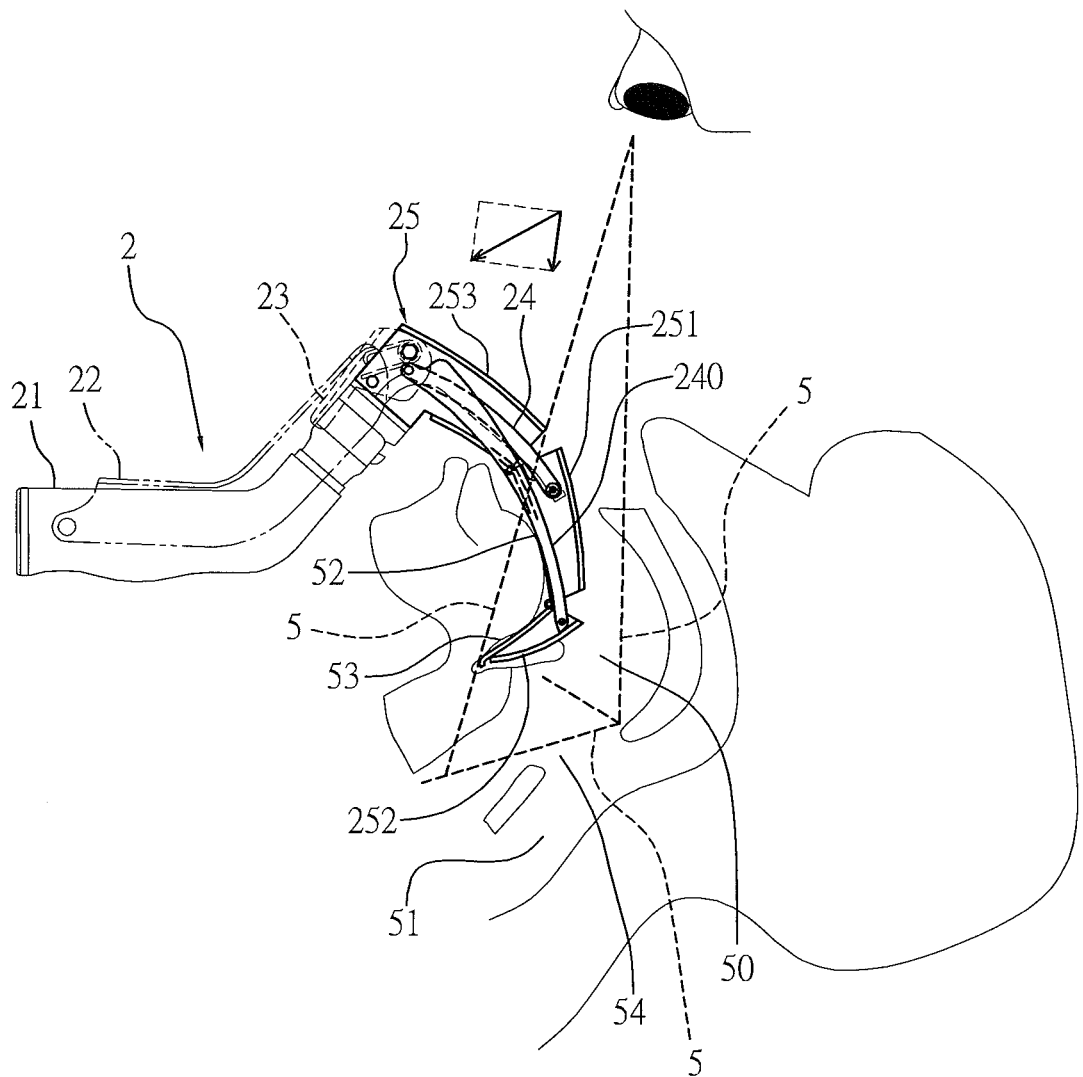
FIG. 7 is a side plan view showing the application of the resistance feedback laryngoscope according to the preferred embodiment of the present invention.

Also, as shown in FIG. 7, in the intubating operation, the mouth 5 is expended so as to see a pharynx 50, and then the laryngoscope 2 is inserted into the throat 51. Thereafter, the user holds the pushing grip 21 and places the two-step blade 25 into the mouth 5, such that the laryngoscope 2 pushes the mouth 5 by ways of the curved front side of the pushing grip 21, thereafter as having a laryngoscopy, the pushing grip 21 is pushed further so that the first movable blade 251 presses a tongue 52, such that the pharynx 50 is seen distinctly, and then the trigger pad 22 presses the rotary shaft 23 to swing, such that the first transmitting rod 24 and the second transmitting rod 240 are driven so that the first movable blade 251 and the second movable blade 252 curve and raise upwardly to further press an epiglottis 53 to retract backwardly, hence the mouth 5 and a glottis 54 form a straight line, thus seeing the throat 51 clearly. Furthermore, the laryngoscope 2 is applied in the intubating operation to lower a damage of the patient's teeth.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A resistance feedback laryngoscope comprising:
a pushing grip, a trigger pad, a rotary shaft, a first transmitting rod, a second transmitting rod, and a two-step levering blade, the pushing grip including a curved front side, and a bottom end of the curved front side of the pushing grip connecting with the blade set, the two-step levering blade including a first movable blade fixed on a middle section thereof, a second movable blade mounted on a front end thereof, and a fixed blade, the fixed blade coupling with the first transmitting rod and the second transmitting rod, and a front end of the first transmitting rod being coupled with the first movable blade, a front end of the second transmitting rod being connected with the second movable blade, such that the first movable blade and the second movable blade are pushed by the first transmitting rod and the second transmitting rod to raise curvedly; the first transmitting rod and the second transmitting rod connecting with the rotary shaft, the rotary shaft being fixed on a drive post, and the drive post having a resilient element fitted therein, the resilient element having a first foot and a second foot, the first foot of the resilient element abutting against a locking peg proximate to the drive post, and the second foot being biased against a side piece of the rotary shaft; the trigger pad contacting with two sides of an outer wall of the pushing grip and curving upward slightly, and the trigger pad including an arcuate groove formed therein, a bottom end of the arcuate groove contacting with the side piece of the rotary shaft.

2. The resistance feedback laryngoscope of as claimed in claim 1, wherein the first movable blade and the second movable blade raise upwardly, and then the trigger pad presses the side piece of the rotary shaft to swing, such that the first transmitting rod and the second transmitting rod are driven so that the first movable blade and the second movable blade curve at an angle, and wherein the force applied on the trigger pad comes from the natural gripping force during direct laryngoscopy, which is directly proportional to the tissue resistance.

3. The resistance feedback laryngoscope as claimed in claim 1, wherein the first movable blade, the second movable blade, and the fixed blade are pivoted together by using a plurality of first bolts so that the first movable blade and the second movable blade swing, wherein a length of each first bolt is within 2 to 4 cm, and wherein the first movable blade provides the adjustability of blade curve to the anatomy of patients, and the second movable blade assists in elevating the larynx.

4. The resistance feedback laryngoscope as claimed in claim 1, wherein the first transmitting rod is coupled with the first movable blade by using one of three positioning knobs, and the second transmitting rod is connected with the second movable blade by ways of another of the three positioning knobs.

* * * * *